United States Patent
Zhong et al.

(10) Patent No.: US 10,966,993 B2
(45) Date of Patent: Apr. 6, 2021

(54) PHARMACEUTICAL COMPOSITION COMPRISING A SULFONYLUREA DRUG AND PREPARATION METHOD THEREOF

(71) Applicant: JIANGSU AOSAIKANG PHARMACEUTICAL CO., LTD., Nanjing (CN)

(72) Inventors: Wu Zhong, Beijing (CN); Chunsheng Gao, Beijing (CN); Wei Gong, Beijing (CN); Song Li, Beijing (CN); Hongyu Chen, Nanjing (CN)

(73) Assignee: JIANGSU AOSAIKANG PHARMACEUTICAL CO., LTD., Nanjing (CN)

( * ) Notice: Subject to any disclaimer, the term of this patent is extended or adjusted under 35 U.S.C. 154(b) by 0 days.

(21) Appl. No.: 16/469,124

(22) PCT Filed: Dec. 13, 2017

(86) PCT No.: PCT/CN2017/115993
§ 371 (c)(1),
(2) Date: Jun. 12, 2019

(87) PCT Pub. No.: WO2018/108111
PCT Pub. Date: Jun. 21, 2018

(65) Prior Publication Data
US 2020/0022993 A1 Jan. 23, 2020

(30) Foreign Application Priority Data
Dec. 14, 2016 (CN) .......................... 201611149802.4

(51) Int. Cl.
| | | |
|---|---|---|
| *A61K 31/64* | (2006.01) | |
| *A61P 3/10* | (2006.01) | |
| *A61K 47/02* | (2006.01) | |
| *A61K 47/26* | (2006.01) | |
| *A61K 47/40* | (2006.01) | |
| *A61K 9/00* | (2006.01) | |
| *A61K 9/08* | (2006.01) | |
| *A61K 9/19* | (2006.01) | |

(52) U.S. Cl.
CPC .............. *A61K 31/64* (2013.01); *A61K 47/02* (2013.01); *A61K 47/26* (2013.01); *A61K 47/40* (2013.01); *A61P 3/10* (2018.01); *A61K 9/0019* (2013.01); *A61K 9/08* (2013.01); *A61K 9/19* (2013.01)

(58) Field of Classification Search
CPC ..................................................... A61K 31/64
See application file for complete search history.

(56) References Cited

U.S. PATENT DOCUMENTS

| | | | |
|---|---|---|---|
| 5,773,029 A | 6/1998 | Chiesi et al. | |
| 2005/0058705 A1* | 3/2005 | Remon | A61K 9/1652 424/464 |
| 2006/0276411 A1* | 12/2006 | Simard | A61K 31/64 514/23 |
| 2011/0034560 A1 | 2/2011 | Jacobson et al. | |
| 2013/0131089 A1 | 5/2013 | Li et al. | |

FOREIGN PATENT DOCUMENTS

| | | | |
|---|---|---|---|
| CN | 1600801 A | 3/2005 | |
| CN | 1823755 A | 8/2006 | |
| CN | 1872231 A | 12/2006 | |
| CN | 101658487 A | 3/2010 | |
| CN | 104644591 A | 5/2015 | |
| JP | 2007-504258 A * | 3/2007 | ............... A61K 9/62 |
| JP | 2011505424 A | 2/2011 | |
| WO | WO 2009/073711 A1 | 6/2009 | |

OTHER PUBLICATIONS

Diaßeta® (glyburide) Tablets USP drug label, available at https://www.accessdata.fda.gov/drugsatfda_docs/label/2009/017532s030lbl.pdf, 2009.*
Cyclobond® Handbook, A Guide to Using Cyclodextrin Bonded Phases for Chiral LC Separations, 6th ed., © 2002 Advanced Separation Technologies, Inc., p. 1-58, at p. 42-45.*
Armstrong et al., Separation of Drug Stereoisomers by the Formation of-Cyclodextrin Inclusion Complexes, Science, vol. 232, p. 1132-1135, May 30, 1986.*
Kasetti et al., Conformational polymorphism in sulfonylurea drugs: electronic structure analysis, J. Phys. Chem. B 2010, 114, 35, 11603-11611.*
Yang et al., "Study on the Enhancing Solubility of HP-β-CD with Gliclazide by Phase Solubility Method", Journal of Analytical Science, Jun. 2004, 20(3): 331-332.
Redenti et al., "Cyclodextrin Complexes of Salts of Acidic Drugs. Thermodynamic Properties, Structural Features, and Pharmaceutical Applications", Journal of Pharmaceutical Sciences, 2001, 90(8): 979-986.

* cited by examiner

*Primary Examiner* — Svetlana M Ivanova
(74) *Attorney, Agent, or Firm* — James S. Keddie; Bozicevic, Field & Francis LLP

(57) ABSTRACT

An injectable pharmaceutical composition of a sulfonylurea drug and a preparation method thereof were described. The pharmaceutical composition contains a sulfonylurea drug, a cyclodextrin and an additive.

16 Claims, 4 Drawing Sheets

PHARMACEUTICAL COMPOSITION COMPRISING A SULFONYLUREA DRUG AND PREPARATION METHOD THEREOF

CROSS-REFERENCE TO RELATED APPLICATIONS

This application is a § 371 national phase of International Application No. PCT/CN2017/115993, filed on Dec. 13, 2017, which claims benefit of Chinese Patent Application No. 201611149802.4, filed on Dec. 14, 2016, which applications are incorporated by reference herein.

TECHNICAL FIELD

The present invention relates to the field of pharmaceutical, especially relates to a pharmaceutical composition for injection containing a sulfonylurea drug and the preparation method thereof.

BACKGROUND

A Sulfonylurea drug is an insulin secretagogue, which is widely used in the clinical treatment of type II diabetes. Widely used sulfonylurea drugs in clinical practice include glibenclamide (also referred to as gliburide), gliclazide, glipizide, gliquidone, glibornuride, glimepiride, etc. All the hypoglycemic sulfonylurea drugs in the market are oral solid preparations.

Formula 1

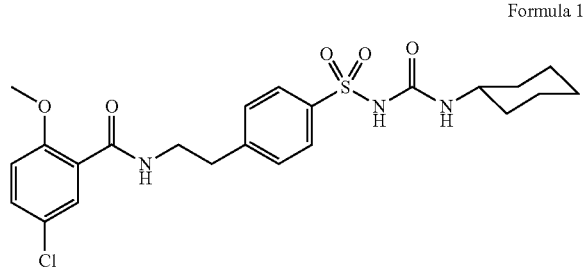 [SMILES: COc1ccc(Cl)cc1C(=O)NCCc1ccc(S(=O)(=O)NC(=O)NC2CCCCC2)cc1]

Studies in recent years have shown that glibenclamide (Formula 1, also referred to as Glyburide, whose chemical name is 5-chloro-N-(4-[N-(cyclohexylcarbamoyl)aminosulfonyl]phenethyl)-2-methoxybenzamide) could be used for the prevention of cerebral edema for patients with stroke when administered by intravenous injection (Sheth et.al, Pilot study of intravenous glyburide in patients with a large ischemic stroke. Stroke, 2014, 45:281~283). Sulfonylurea drugs exert their effects by acting on sulfonylurea receptors (SURs). Sulfonylurea drugs are mildly acidic, and has poor solubility in water, especially poor solubility at neutral and acidic pH. Glibenclamide has a water solubility of less than 5 μg/ml. It was reported by Schrage et.al. that an injectable solution containing 1 mg/ml of glibenclamide was prepared by using a 0.1M NaOH solution (Schrage et.al, Effects of combined inhibition of ATP-sensitive potassium channels, nitric oxide, and prostaglandins on hyperemia during moderate exercise. J Appl Physiol, 2006, 100:1506-1512). However, the pH of this solution was up to 11, which is beyond the usual pH range for injection (pH4~pH9). If an acidic pH regulator was used to reduce the pH, there may be a risk of drug precipitation. Moreover, for a solution with a low concentration of glibenclamide, there is an apparent adsorption of drug onto PVC infusion bags.

SUMMARY OF THE INVENTION

The present disclosure provides a novel sulfonylurea-contained drug, especially a glibenclamide-contained injectable composition, which further contains an additive and a cyclodextrin. It was surprisingly found by the inventor that, compared with the composition in prior art in which either a cyclodextrin or an additive is solely used, the composition, in which a cyclodextrin and an additive are used in combination, sparingly improves the solubility and stability of sulfonylurea drugs in water, as well as significantly inhibits the adsorption of glibenclamide in a PVC infusion bag.

In one aspect, the present disclosure provides a pharmaceutical composition comprising a sulfonylurea drug, a cyclodextrin and an additive.

In an embodiment, any of the pharmaceutical compositions according to the present disclosure has a weight ratio of the additive to the cyclodextrin of 1:0.1~4000, for example 1:1~400, for example 1:1~100, for example 1:1~50, for example 1:5~50, for example 1:50~400, for example 1:1~10, for example 1:1~8, for example 1:1~6, for example 1:1~4, for example 1:6~8;

preferably, the additive is meglumine, and the weight ratio of the additive to the cyclodextrin is 1:1~400;

preferably, the additive is sodium carbonate, and the weight ratio of the additive to the cyclodextrin is 1:50~400;

preferably, the additive is sodium hydroxide, and the weight ratio of the additive to the cyclodextrin is 1:50~4000;

preferably, the additive is sodium hydrogen carbonate, and the weight ratio of the additive to the cyclodextrin is 1:0.1~10.

In an embodiment, any of the pharmaceutical compositions according to the present disclosure has a weight ratio of the sulfonylurea drug to the additive of 1:0.01~100, for example 1:0.05~100, for example 1:0.5~100, for example 1:1~50, for example 1:1~10.

In an embodiment, any of the pharmaceutical compositions according to the present disclosure has a weight ratio of the sulfonylurea drug to the cyclodextrin of 1:0.2~1000, for example 1:25~250, for example 1:0.5~100, for example 1:1~50, for example 1:1~10.

In an embodiment, any of the pharmaceutical compositions according to the present disclosure, the weight ratio of the sulfonylurea drug:the additive:the cyclodextrin is 1:0.05~100:0.2~1000, for example 1:0.5~50:25~250, for example 1:0.1~20:10~100.

In an embodiment, the sulfonylurea drugs are compounds that stimulate insulin secretion of pancreatic β cells by delivering signals via sulfonylurea receptors in cell membranes.

In an embodiment, in any of the pharmaceutical compositions according to the present disclosure, the sulfonylurea drug is selected from glibenclamide, gliclazide, glipizide, gliquidone, glibornuride, glimepiride, glisoxepide, acetohexamide, glycyclamide, glisamuride, glisentide, glisolamide, glyoctamide, chlorpropamide, tolazamide, tolbutamidum, repaglinide and nateglinide;

preferably, the sulfonylurea drug is glibenclamide.

In an embodiment, in any of the pharmaceutical compositions according to the present disclosure, the cyclodextrin is selected from α-cyclodextrin, β-cyclodextrin, γ-cyclodextrin and pharmaceutically acceptable cyclodextrin derivatives;

preferably, the pharmaceutically acceptable cyclodextrin derivative is selected from dimethyl-β-cyclodextrin, 2-hydroxyethyl-β-cyclodextrin, 2-hydroxypropyl-β-cyclodextrin, 3-hydroxypropyl-β-cyclodextrin, sulfobutyl ether-β-cyclodextrin and trimethyl-β-cyclodextrin;

preferably, the cyclodextrin is selected from β-cyclodextrin, dimethyl-β-cyclodextrin, 2-hydroxyethyl-β-cyclodextrin, 2-hydroxypropyl-β-cyclodextrin, 3-hydroxypropyl-β-cyclodextrin, sulfobutyl ether-β-cyclodextrin and trimethyl-β-cyclodextrin;

further preferably, the cyclodextrin is 2-hydroxypropyl-β-cyclodextrin, 3-hydroxypropyl-β-cyclodextrin and/or sulfobutyl ether-β-cyclodextrin;

further preferably, the cyclodextrin is 2-hydroxypropyl-β-cyclodextrin.

According to Pharmacopoeia of the People's Republic of China, in the absence of special instructions, hydroxypropyl-β-cyclodextrin in the present disclosure refers to 2-hydroxypropyl-β-cyclodextrin.

In an embodiment, in any of the pharmaceutical compositions according to the present disclosure, the additive is selected from sodium carbonate, sodium hydrogen carbonate, sodium borate, sodium hydroxide, potassium hydroxide, disodium hydrogen phosphate, sodium dihydrogen phosphate, sodium dihydrogen citrate, sodium monohydrogen citrate, sodium citrate, meglumine, tris(hydroxymethyl)aminomethane, monoethanolamine, diethanolamine, lysine, arginine and histidine.

Preferably, the additive is selected from sodium hydroxide, sodium carbonate, sodium hydrogen carbonate, sodium borate and meglumine;

preferably, the additive is sodium carbonate, sodium hydrogen carbonate, sodium hydroxide and/or meglumine;
  preferably, the additive is sodium carbonate;
  preferably, the additive is sodium hydrogen carbonate;
  preferably, the additive is sodium hydroxide;
  preferably, the additive is meglumine.

In an embodiment, any of the pharmaceutical compositions according to the present disclosure further comprises glucose, sodium chloride, a lyophilization additive (e.g., mannitol, lactose or gelatin), a pH regulator (e.g., hydrochloric acid) and/or water.

In an embodiment, the lyophilization additive is a substance capable of preventing active substances from impairment or degeneration during the process of freezing or storage, for example, preventing active substances from sublimating or dissipating with steam, and allowing active constituent of the active substances to form a solid.

In an embodiment, the pH regulator refers to a substance that is capable of adjusting a solution's pH to a desired range, examples of which includes an inorganic acid, an inorganic base, an organic acid, an organic base and the buffered salt systems thereof, and those commonly used are sodium hydroxide, hydrochloric acid, glycine, hydrofluoric acid, triethylamine, acetic acid, phosphoric acid, malic acid, citric acid, acetic acid buffered salt, phosphoric acid buffered salt and the like, as well as aqueous solutions of them.

In an embodiment, any of the pharmaceutical compositions according to the present disclosure is an injection, preferably an injectable solution (e.g., an aqueous injectable solution) or a powder injection.

In an embodiment, any of the pharmaceutical compositions according to the present disclosure is an injectable solution (e.g., an aqueous injectable solution);

preferably, the pharmaceutical composition comprises a cyclodextrin at a concentration of 0.5%~40% (w/v), for example 1%~40% (w/v), for example 2.5%~40% (w/v), for example 5%~20% (w/v), for example 1%~5% (w/v);

preferably, the pharmaceutical composition comprises an additive at a concentration of 0.01%~20% (w/v), for example 0.01%~15% (w/v), for example 0.01%~10% (w/v), for example 0.01%~5% (w/v), for example 0.1%~5% (w/v), for example 0.03%~5% (w/v), for example 0.2%~4% (w/v), for example 0.1%~1% (w/v);

preferably, the pharmaceutical composition comprises a cyclodextrin at a concentration of 0.5%~40% (w/v), for example 1%~40% (w/v), for example 2.5%~40% (w/v), for example 5%~20% (w/v), for example 1%~5% (w/v); wherein the pharmaceutical composition comprises an additive at a concentration of 0.01%~20% (w/v), for example 0.01%~15% (w/v), for example 0.01%~10% (w/v), for example 0.01%~5% (w/v), for example 0.1%~5% (w/v), for example 0.2%~4% (w/v), for example 0.1%~1% (w/v);

further preferably, the pharmaceutical composition comprises a sulfonylurea drug at a concentration of less than or equal to the saturation concentration of the sulfonylurea drug in the injectable solution; further preferably the pharmaceutical composition comprises an additive at a concentration of 0.01~50 mg/ml, for example 0.01~10 mg/ml, for example 0.01~5 mg/ml, for example 0.01~2.5 mg/ml, for example 0.01~2 mg/ml.

Sulfonylurea drugs could be dissolved in an aqueous solution comprising an additive and a cyclodextrin by one skilled in the art as required, with a sulfonylurea drug concentration being less than or equal to the saturation concentration of the sulfonylurea drug. The saturation concentration refers to the concentration of the sulfonylurea drug in a saturated solution thereof (unit: mg/ml).

In an embodiment, any of the pharmaceutical compositions according to the present disclosure characterized in one or more of the following items:

a) the pharmaceutical composition comprises an additive at a concentration of 0.01~0.5% (w/v), a cyclodextrin at a concentration of 0.5~10% (w/v), a sulfonylurea drug at a concentration of less than or equal to the saturation concentration of the sulfonylurea drug in the injectable solution (preferably, a sulfonylurea drug at a concentration of 0.01~3 mg/ml, for example 0.1~3 mg/ml, for example 1~3 mg/ml);

b) the pharmaceutical composition comprises an additive at a concentration of 0.1~0.5% (w/v), a cyclodextrin at a concentration of 0.5~10% (w/v), a sulfonylurea drug at a concentration of less than or equal to the saturation concentration of the sulfonylurea drug in the injectable solution (preferably, a sulfonylurea drug at a concentration of 0.01~3 mg/ml, for example 0.1~3 mg/ml, for example 1~3 mg/ml);

c) the pharmaceutical composition comprises an additive at a concentration of 0.1~0.3% (w/v), a cyclodextrin at a concentration of 1~5% (w/v), a sulfonylurea drug at a concentration of less than or equal to the saturation concentration of the sulfonylurea drug in the injectable solution (preferably, a sulfonylurea drug at a concentration of 0.01~2.5 mg/ml, for example 0.1~2.5 mg/ml, for example 1~2.5 mg/ml);

d) the pharmaceutical composition comprises an additive at a concentration of 1~10% (w/v), a cyclodextrin at a concentration of 1~30% (w/v), a sulfonylurea drug at a concentration of less than or equal to the saturation concentration of the sulfonylurea drug in the injectable solution (preferably, a sulfonylurea drug at a concentration of 0.01~50 mg/ml, for example 0.1~50 mg/ml, for example 10~50 mg/ml);

e) the pharmaceutical composition comprises an additive at a concentration of 4~6% (w/v), a cyclodextrin at a concentration of 5~20% (w/v), a sulfonylurea drug at a concentration of less than or equal to the saturation concentration of the sulfonylurea drug in the injectable solution (preferably, a sulfonylurea drug at a concentration of 0.01~50 mg/ml, for example 0.1~50 mg/ml, for example 25~50 mg/ml).

In an embodiment, any of the pharmaceutical compositions according to the present disclosure is obtained by drying (e.g., freeze drying) any injectable solution of the disclosure.

In an embodiment, any of the pharmaceutical compositions according to the present disclosure has a pH of 5~11, preferably 6~10, preferably 7~9, more preferably 7~8.

In a further aspect, the present disclosure provides a method for preparing any of the pharmaceutical compositions according to the present disclosure, which includes the following steps:
a) dissolving the additive and the cyclodextrin in a solvent;
b) adding the sulfonylurea drug into the product of step a), mixing by stirring;
c) optionally, adding a lyophilization additive into the product of step b), and adjusting pH;
d) subjecting the product of step b) or c) to sterilization, optionally, subjecting the product of step d) to drying, obtaining the desired composition; preferably, the drying is freeze drying;
preferably, the solvent is water, physiological saline or a glucose solution.

In a further aspect, the present disclosure provides a use of any of the pharmaceutical compositions according to the present disclosure in the manufacture of a medicament for the prophylactic and/or therapeutic treatment of acute stroke, neurologic impairment, traumatic brain injury, encephaledema, spinal cord injury, myocardial infarction, shock, organ ischemia, ventricular arrhythmias, type I diabetes or type II diabetes.

In a further aspect, the present disclosure provides a method for the prophylactic and/or therapeutic treatment of acute stroke, neurologic impairment, traumatic brain injury, encephaledema, spinal cord injury, myocardial infarction, shock, organ ischemia, ventricular arrhythmias, type I diabetes or type II diabetes, comprising administering to a subject in need thereof a therapeutically and/or prophylactically effective amount of any of the pharmaceutical compositions according to the present disclosure.

In an embodiment, the method of administering to the subject in need thereof the pharmaceutical composition includes oral administration or injection, for example injection.

In an embodiment, the term "a therapeutically effective amount" is defined as an amount that is sufficient to cure, alleviate or partially inhibit the given disease as well as clinical manifestations of the disease. An amount suitable for achieving this purpose is defined as "therapeutically effective amount". The effective amount for each purpose depends on the severity of the disease or injury and the weight of the subject and the general health thereof. It should be understood that the determination of suitable doses could be determined by routine experiments that establishing a numerical matrix and testing different points in the matrix, all of which are within the common practice of well-trained physicians or veterinarians.

In a further aspect, the present disclosure provides any of the pharmaceutical compositions according to the present disclosure for use in the prophylactic and/or therapeutic treatment of acute stroke, neurologic impairment, traumatic brain injury, encephaledema, spinal cord injury, myocardial infarction, shock, organ ischemia, ventricular arrhythmias, type I diabetes or type II diabetes.

In an embodiment, the method for preparing any of the pharmaceutical compositions according to the present disclosure includes the following steps:
a) dissolving the additive and the cyclodextrin in water, mixing uniformly;
b) adding the active ingredient, the sulfonylurea drug, into the product of step a), stirring;
c) adjusting the pH of the product of step b);
d) subjecting the resulting solution of step c) to an aseptic filtration or a hot-pressed sterilization;
e) dispensing the product of step d) in tubular vials or ampoules, then sealing/capping.

In another embodiment, the method for preparing any of the pharmaceutical compositions according to the present disclosure includes the following steps:
a) dissolving the additive and the cyclodextrin in water, mixing uniformly;
b) adding the active ingredient, the sulfonylurea drug, into the product of step a), stirring;
c) adding a lyophilization additive into the product of step b), adjusting pH;
d) dispensing the product of step c) in vials or ampoules;
e) removing water from the resulting solution of step d) by freeze drying, then sealing/capping.

In a specific embodiment, the method for preparing any of the pharmaceutical compositions according to the present disclosure includes the following steps:
a) dissolving the additive (e.g., selected from one or more of the following: sodium carbonate, sodium hydrogen carbonate, sodium borate, sodium hydroxide, potassium hydroxide, disodium hydrogen phosphate, sodium dihydrogen phosphate, sodium dihydrogen citrate, sodium monohydrogen citrate, sodium citrate, meglumine, Tris(hydroxymethyl)aminomethane, monoethanolamine, diethanolamine, lysine, arginine and histidine), the cyclodextrin (e.g., selected from one or more of α-cyclodextrin, β-cyclodextrin, γ-cyclodextrin, and the pharmaceutically acceptable cyclodextrin derivatives) in water with stirring;
b) further adding active ingredients, the sulfonylurea drug (e.g., selected from one or more of the following: glibenclamide, gliclazide, glipizide, gliquidone, glibornuride, glimepiride, glisoxepide, acetohexamide, glycyclamide, glisamuride, glisentide, glisolamide, glyoctamide, chlorpropamide, tolazamide, tolbutamidum, repaglinide, nateglinide), dissolving by stirring, then the product is obtained.

In an embodiment, the term "additive" refers to a substance capable of interacting with the active ingredient, thus enhancing the inclusion efficiency of the cyclodextrin, further improving the solubility of the drug.

In an embodiment, the additive doesn't include cyclodextrin.

In an embodiment, the term "pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient.

In an embodiment, the term composition is used in the meaning of a mixture of two or more substance, which is commonly recognized in the present technical field. Hence, in addition to the above active agents and additives, other excipients, buffering agents or pH regulators, osmotic pressure regulators, preservatives, antioxidants and the like, which are commonly used in the present technical field, may also be comprised in the composition, as long as for the purpose of the present invention.

In an embodiment, the pharmaceutical composition may be formulated into any dosage forms with pharmaceutically acceptable excipients, for example an oral preparation or an injection, an oral preparation may be for example a tablet, a capsule, a granule, an oral solution, and an injection maybe for example an aqueous injection or a lyophilized powder injection.

In an embodiment, an injection is a preparation that may be injected into the body of a patient, without any limitation of its dosing route, dosing site, dosing means and the like, while the preparations that are administered intravenously, intra-arterially, and intravesically are especially considered.

In an embodiment, the composition of the present invention may be dissolved in physiological saline to produce an injection, while it also may be dissolved in water for injection or glucose injections to produce an injection.

In an embodiment, physiological saline, water for injection, glucose injections all conform to the specification of the Pharmacopoeia of People's Republic of China.

It is understood that the terms "a", "an" and "the" and similar terms used in the present disclosure should involves singles and pluralities, unless otherwise indicated in the application or significantly conflict in the context.

In the present disclosure, the concentration "%" or "% (w/v)" of the additive and the cyclodextrin refers to the mass volume concentration, indicating the grams of the solute contained per 100 ml solution, for example 20% (w/v) indicates that there is 20 g solute per 100 ml solution.

Compared with the prior art, the pharmaceutical composition of the present disclosure has one or more of the following beneficial effects:

1) distinctly enhancing the water solubility of sulfonylurea drugs, especially in a neutral or acidic aqueous solution;

2) distinctly enhancing the stability of the pharmaceutical composition, with little drug precipitation, especially in a neutral or acidic aqueous solution;

3) significantly inhibiting drug absorption in a PVC infusion bag;

4) the prescription is simple and the quality is stable;

5) the preparation method has good reproducibility, convenient to operate, and with high controllability;

6) may significantly improve the neurologic impairment, for example a neurobehavioral deficient caused by cerebral infarction.

BRIEF DESCRIPTION OF THE DRAWINGS

FIG. 1~FIG. 7 are the solubility curves of glibenclamide in different solutions at 25° C., wherein:

FIG. 1 is the solubility curve of glibenclamide in a solution only comprising meglumine;

FIG. 2 is the solubility curve of glibenclamide in a solution only comprising 2-hydroxypropyl-β-cyclodextrin;

FIG. 3 is the solubility curve of glibenclamide in a solution comprising 2-hydroxypropyl-β-cyclodextrin and meglumine (the concentration of meglumine is 0.1%);

FIG. 4 is the solubility curve of glibenclamide in a solution comprising 2-hydroxypropyl-β-cyclodextrin and meglumine (the concentration of meglumine is 5%);

FIG. 5 is the solubility curve of glibenclamide in a solution comprising both 2-hydroxypropyl-β-cyclodextrin and sodium carbonate (the concentration of sodium carbonate is 0.1%);

FIG. 6 is the solubility curve of glibenclamide in a solution comprising both 2-hydroxypropyl-β-cyclodextrin and sodium hydrogen carbonate (the concentration of sodium hydrogen carbonate is 4%);

FIG. 7 is the solubility curve of glibenclamide in a solution comprising both 2-hydroxypropyl-β-cyclodextrin and sodium hydroxide (the concentration of sodium hydroxide is 0.01%);

Figure 1:
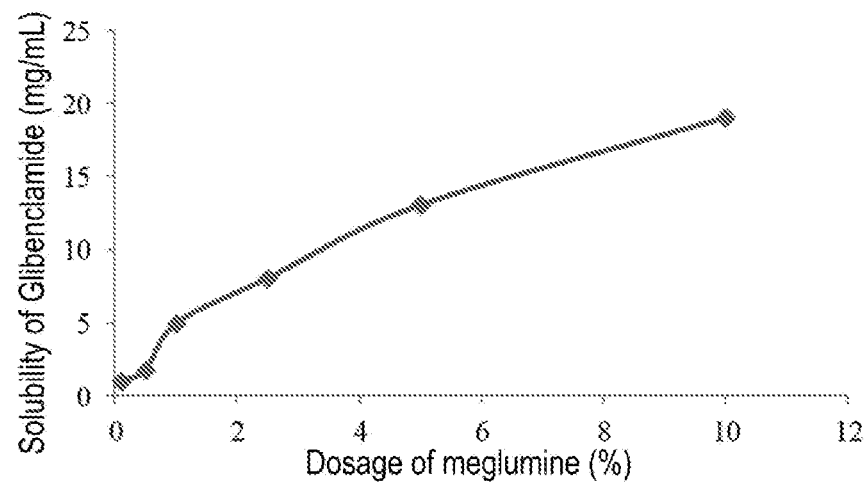

In the figures, MEG refers to meglumine.

DETAILED DESCRIPTION

Examples of the present disclosure will be described below in greater detail in combination with examples, however, it would be understood by those skilled in the art that, the following examples and Test Examples are only for the purpose of illustrating the present disclosure, and are not to be construed as limiting the scope of the present disclosure. The examples and Test Examples will be carried out according to normal conditions or conditions suggested by the manufacturer if there were no special illustrations, and the reagents or instruments used are all commercially available normal products if there were no manufacturers noted.

In the following examples, the additive is meglumine, sodium carbonate, sodium hydroxide or sodium hydrogen carbonate described in the formula.

EXAMPLE 1

Preparation of Glibenclamide Injectable Composition

| Formula | | |
|---|---|---|
| Ingredients | Dosage (g/100 ml) | Specification |
| Glibenclamide | 0.2 | Concentration of the active ingredient 2 mg/ml |
| Meglumine | 0.1 | Concentration of the additive 0.1% (w/v) |
| Hydroxypropyl-β-cyclodextrin | 5.0 | Concentration of the cyclodextrin 5% (w/v) |
| Water | Add to 100 ml | — |

Preparation method: According to the formula, the additive and the cyclodextrin were dissolved in 50~70 ml water, into which was added the glibenclamide powder, with stirring to dissolve, obtaining a solution. The above solution was adjusted to pH 7.0 with 0.1 M hydrochloric acid, and added to 100 ml with water, obtaining a glibenclamide injectable composition.

EXAMPLE 2

Preparation of Glibenclamide Injectable Composition

| Ingredients | Dosage (g/100 ml) | Specification |
|---|---|---|
| | Formula: | |
| Glibenclamide | 0.1 | Concentration of the active ingredient 1 mg/ml |
| Meglumine | 0.1 | Concentration of the additive 0.1% (w/v) |
| Hydroxypropyl-β-cyclodextrin | 5.0 | Concentration of the cyclodextrin 5.0% (w/v) |
| Water | Add to 100 ml | — |

In Example 2, the method for preparing the composition was similar to that of Example 1, with a difference in that the solution formulated according to the formula in Example 2 was adjusted to pH 8.0.

EXAMPLE 3

Preparation of Glibenclamide Injectable Composition

| Ingredients | Dosage (g/100 ml) | Specification |
|---|---|---|
| | Formula: | |
| Glibenclamide | 0.01 | Concentration of the active ingredient 0.1 mg/ml |
| Meglumine | 0.1 | Concentration of the additive 0.1% (w/v) |
| Hydroxypropyl-β-cyclodextrin | 2.5 | Concentration of the cyclodextrin 2.5% (w/v) |
| Water | Add to 100 ml | — |

In Example 3, the method for preparing the composition was similar to that of Example 1, with a difference in that the solution formulated according to the formula in Example 3 was adjusted to pH 7.5.

EXAMPLE 4

Preparation of Glibenclamide Injectable Composition

| Ingredients | Dosage (g/100 ml) | Specification |
|---|---|---|
| | Formula: | |
| glibenclamide | 0.001 | Concentration of the active ingredient 0.01 mg/ml |
| Meglumine | 0.1 | Concentration of the additive 0.1% (w/v) |
| Hydroxypropyl-β-cyclodextrin | 1.0 | Concentration of the cyclodextrin 1.0% (w/v) |
| Water | Add to 100 ml | — |

In Example 4, the method for preparing the composition was similar to that of Example 1, with a difference in that the solution formulated according to the formula in Example 4 was adjusted to pH 9.0.

EXAMPLE 5

Preparation of Glibenclamide Injectable Composition

| Ingredients | Dosage (g/100 ml) | Specification |
|---|---|---|
| | Formula: | |
| glibenclamide | 0.2 | Concentration of the active ingredient 2 mg/ml |
| Meglumine | 0.1 | Concentration of the additive 0.1% (w/v) |
| Hydroxypropyl-β-cyclodextrin | 10.0 | Concentration of the cyclodextrin 10% (w/v) |
| Water | Add to 100 ml | — |

In Example 5, the method for preparing the composition was similar to that of Example 1.

EXAMPLE 6:

Preparation of glibenclamide injectable composition

| Ingredients | Dosage (g/100 ml) | Specification |
|---|---|---|
| | Formula: | |
| glibenclamide | 0.1 | Concentration of the active ingredient 1 mg/ml |
| Meglumine | 0.1 | Concentration of the additive 0.1% (w/v) |
| Hydroxypropyl-β-cyclodextrin | 20.0 | Concentration of the cyclodextrin 20% (w/v) |
| Water | Add to 100 ml | — |

In Example 6, the method for preparing the composition was similar to that of Example 1, with a difference in that the solution formulated according to the formula in Example 6 was adjusted to pH 6.5.

EXAMPLE 7

Preparation of Glibenclamide Injectable Composition

| Ingredients | Dosage (g/100 ml) | Specification |
|---|---|---|
| | Formula: | |
| glibenclamide | 0.2 | Concentration of the active ingredient 2 mg/ml |
| Meglumine | 0.1 | Concentration of the additive 0.1% (w/v) |

-continued

| Ingredients | Dosage (g/100 ml) | Specification |
|---|---|---|
| Hydroxypropyl-β-cyclodextrin | 40.0 | Concentration of the cyclodextrin 40% (w/v) |
| Water | Add to 100 ml | — |

In Example 7, the method for preparing the composition was similar to that of Example 1, with a difference in that the solution formulated according to the formula in Example 7 was adjusted to pH 6.0.

EXAMPLE 8

Preparation of Glibenclamide Injectable Composition

| Ingredients | Dosage (g/100 ml) | Specification |
|---|---|---|
| glibenclamide | 0.2 | Concentration of the active ingredient 2.0 mg/ml |
| Anhydrous sodium carbonate | 0.1 | Concentration of the additive 0.1% (w/v) |
| Hydroxypropyl-β-cyclodextrin | 5.0 | Concentration of the cyclodextrin 5% (w/v) |
| Water | Add to 100 ml | — |

In Example 8, the method for preparing the composition was similar to that of Example 1, with a difference in that the solution formulated according to the formula in Example 8 was adjusted to pH 7.5.

EXAMPLE 9

Preparation of Glibenclamide Injectable Composition

| Ingredients | Dosage (g/100 ml) | Specification |
|---|---|---|
| glibenclamide | 0.1 | Concentration of the active ingredient 1.0 mg/ml |
| Sodium hydroxide | 0.2 | Concentration of the additive 0.2% (w/v) |
| Hydroxypropyl-β-cyclodextrin | 5.0 | Concentration of the cyclodextrin 5% (w/v) |
| Water | Add to 100 ml | — |

In Example 9, the method for preparing the composition was similar to that of Example 1, with a difference in that the solution formulated according to the formula in Example 9 was adjusted to pH 7.5.

EXAMPLE 10

Preparation of Glibenclamide Injectable Composition

| Ingredients | Dosage (g/100 ml) | Specification |
|---|---|---|
| glibenclamide | 0.1 | Concentration of the active ingredient 1.0 mg/ml |
| Sodium hydrogen carbonate | 4.0 | Concentration of the additive 4.0% (w/v) |
| Hydroxypropyl-β-cyclodextrin | 5.0 | Concentration of the cyclodextrin 5% (w/v) |
| Mannitol | 5.0 | Concentration of the lyophilization additive 5% (w/v) |
| Water | Add to 100 ml | — |

The preparation method was as follows: according to the formula, the additive and the cyclodextrin were dissolved in 50~70 ml water, into which was added the glibenclamide powder, with stirring to dissolve, obtaining a first solution. To the first solution was added the lyophilization additive mannitol, with stirring to dissolve, obtaining a second solution. The second solution was adjusted to pH 7.5 with 0.1 M hydrochloric acid, and adjust volume to 100 ml obtaining a third solution. The third solution was dispensed into vials, freeze-dried according to the lyophilization procedure in Table 1, obtaining the product.

TABLE 1

Lyophilization procedure

| No. | Temperature | Pressure (Pa) | Holding time (hours) |
|---|---|---|---|
| 1 | −40° C. | — | 4 |
| 2 | −30° C. | 14 | 4 |
| 3 | −20° C. | 14 | 2 |
| 4 | −10° C. | 14 | 3 |
| 5 | 0° C. | 14 | 5 |
| 6 | 15° C. | 10 | 2 |
| 7 | 30° C. | 10 | 2 |
| 8 | 30° C. | — | 2 |

EXAMPLE 11

Preparation of Glibenclamide Injectable Composition

| Ingredients | Dosage (g/100 ml) | Specification |
|---|---|---|
| glibenclamide | 0.1 | Concentration of the active ingredient 1 mg/ml |
| sodium carbonate | 1.0 | Concentration of the additive 1.0% (w/v) |
| Hydroxypropyl-β-cyclodextrin | 5.0 | Concentration of the cyclodextrin 5% (w/v) |
| Water | Add to 100 ml | — |

In Example 11, the method for preparing the composition was similar to that of Example 1, with a difference in that the solution formulated according to the formula in Example 11 was adjusted to pH 8.0.

EXAMPLE 12

Preparation of Glibenclamide Injectable Composition

| Ingredients | Dosage (g/100 ml) | Specification |
|---|---|---|
| glibenclamide | 0.1 | Concentration of the active ingredient 1 mg/ml |
| Sodium carbonate | 1.0 | Concentration of the additive 1.0% (w/v) |
| Sulfobutyl ether-β-cyclodextrin | 5.0 | Concentration of the cyclodextrin 5% (w/v) |
| Water | Add to 100 ml | — |

Formula:

In Example 12, the method for preparing the composition was similar to that of Example 1, with a difference in that the solution formulated according to the formula in Example 12 was adjusted to pH 8.0.

EXAMPLE 13

Preparation of Glibenclamide Injectable Composition (Lyophilized Powder Injection The solution prepared in Example 11 was dispensed into vials, 1 ml for each vial. The solution in vials was freeze dried by the lyophilization procedure in Table 1 according to Example 10, obtaining the lyophilized powder injection.

EXAMPLE 14

Preparation of Glibenclamide Injectable Composition (Lyophilized Powder Injection

| Ingredients | Dosage (g/100 ml) | Specification |
|---|---|---|
| glibenclamide | 0.1 | Concentration of the active ingredient 1 mg/ml |
| Sodium hydroxide | 0.03 | Concentration of the additive 0.03% (w/v) |
| Hydroxypropyl-β-cyclodextrin | 5.0 | Concentration of the cyclodextrin 5% (w/v) |
| Water | Add to 100 ml | — |

Formula:

Preparation method: Sodium hydroxide and hydroxypropyl-β-cyclodextrin were dissolved in 80 ml water, into which was added the glibenclamide powder, with stirring to dissolve, obtaining a first solution. To the first solution was added a glycine solution to adjust the solution's pH to 8.8, adjusting volume to 100 ml, obtaining a second solution. The second solution was dispensed into vials, 1 ml for each vial. The second solution in vials was freeze dried, obtaining a lyophilized powder injection. The lyophilized powder injection was an off-white loosened clump.

TEST EXAMPLE 1

Test on the Compatible Stability

This test investigates the compatible stability of the glibenclamide injectable composition with a glucose injection and a physiological saline.

Test method: To 100 ml glucose injection and physiological saline injection were respectively added 1 ml the composition prepared in Example 2, observing the appearance of the injection after 0 h, 24 h, 48 h, 72 h, 96 h, detecting the changes of pH value and relevant substances.

Test results: as shown in Table 2 and Table 3.

TABLE 2

Results of the test on the compatible stability with the glucose injection

| Time | Appearance | pH value | Impurity I[a] (%) | Impurity II[a] (%) | Impurities in total (%) |
|---|---|---|---|---|---|
| 0 h | Clear | 5.45 | 0.17 | 0.26 | 0.52 |
| 24 h | Clear | 5.28 | 0.17 | 0.25 | 0.53 |
| 48 h | Clear | 5.36 | 0.18 | 0.27 | 0.52 |
| 72 h | Clear | 5.44 | 0.18 | 0.28 | 0.54 |
| 96 h | Clear | 5.42 | 0.18 | 0.28 | 0.54 |

TABLE 3

Results of the test on the compatible stability with physiological saline

| Time | Appearance | pH value | Impurity I[a] (%) | Impurity II[a] (%) | Impurities in total (%) |
|---|---|---|---|---|---|
| 0 h | Clear | 5.90 | 0.17 | 0.26 | 0.52 |
| 24 h | Clear | 5.72 | 0.18 | 0.26 | 0.52 |
| 48 h | Clear | 5.79 | 0.18 | 0.28 | 0.54 |
| 72 h | Clear | 5.75 | 0.17 | 0.28 | 0.54 |
| 96 h | Clear | 5.91 | 0.18 | 0.26 | 0.53 |

In tables 2 and 3, [a]Note: Impurity I: 4-[2-(5-chloro-2-methoxybenzamide)-ethyl]-benzenesulfonamide; Impurity II: ethyl 4-[2-(5-chloro-2-methoxybenzamide)-ethyl]-benzenesulfonamido-carboxylate It was shown from the results of Table 2 and Table 3, the compatibilities between the above glibenclamide composition and the glucose injection and the physiological saline are both good.

TEST EXAMPLE 2

Test on the Dilution Stability

Test method: Taking 10 test tubes, and numbering from 1~10. To the 10 test tubes were respectively added 1 ml phosphoric acid buffer which a pH of 7.4. To the test tube No. 1 was then added 1 ml glibenclamide injectable composition prepared in Example 2, shaken to mix the solution uniformly, from which 1 ml solution was then taken to the test tube No. 2. The above operations were repeated until the test tube No. 10, which was left to observe the clarity of the solution in these 10 test tubes.

Test Results: There was no drug anticipation in the 10 test tubes in 96 h, indicating that the compatibility between the composition of this formula and the phosphate buffer with a pH of 7.4 was good.

TEST EXAMPLE 3

Test on the Solubility

An excess amount of glibenclamide powder was added into an aqueous solution comprising different proportion of additive (e.g., meglumine, sodium carbonate, sodium hydrogen carbonate or sodium hydroxide) and cyclodextrin (hydroxypropyl-β-cyclodextrin) to form a suspension. The suspension was placed in a constant shaking incubator, and shaken for 1 h at 25±1° C. The shaken suspension was filtered with a 0.45 μm hydrophilic filter membrane, with the primary filtrate being disposed and the subsequent filtrate being collected. The subsequent filtrate was diluted to appropriate times with a PBS buffer having a pH of 7.4, the absorbance of the diluted subsequent filtrate was determined at a wavelength of 225 nm, and the solubility of glibenclamide in the diluted subsequent filtrate was calculated according to the absorbance. Corresponding solubility curves were plotted with the solubility of glibenclamide as the vertical axis and the concentration of cyclodextrin and/or meglumine as the horizontal axis. Test results: the solubility curves of glibenclamide at 25° C. were seen in FIG. 1 to FIG. 7; the corresponding solubility data was seen in Table 4 to Table 10.

FIG. 1 is the solubility curve of glibenclamide in a solution only comprising meglumine, Table 4 is the corresponding solubility data. As can be seen from FIG. 1, the water solubility of glibenclamide goes up as the concentration of meglumine increases: the concentration of meglumine ranges from 0.1% (w/v) to 10% (w/v), the water solubilities of glibenclamide at 25° C. are respectively 0.96 mg/ml to 19.05 mg/ml.

TABLE 4

| No. | Concentration of meglumine (%, w/v) | Concentration of cyclodextrin (%, w/v) | Solubility (mg/ml) |
| --- | --- | --- | --- |
| 1 | 0.1 | 0 | 0.96 |
| 2 | 0.5 | 0 | 1.76 |
| 3 | 1 | 0 | 4.93 |
| 4 | 2.5 | 0 | 8.03 |
| 5 | 5 | 0 | 13.05 |
| 6 | 10 | 0 | 19.05 |

Figure 2:
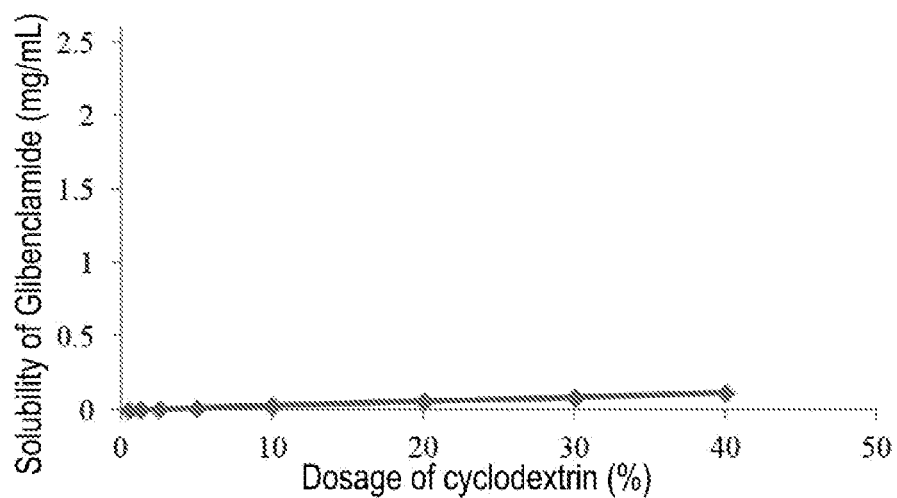

FIG. 2 is the solubility curve of glibenclamide in a solution only comprising 2-hydroxypropyl-β-cyclodextrin, Table 5 is the corresponding solubility data. As can be seen from FIG. 2: the water solubility of glibenclamide goes up linearly as the concentration of cyclodextrin increases: as the concentration of cyclodextrin ranges from 0.5% (w/v) to 40% (w/v), the water solubilities of glibenclamide at 25° C. are respectively 0.0013 mg/ml to 0.12 mg/ml.

TABLE 5

| No. | Concentration of meglumine (%, w/v) | Concentration of cyclodextrin (%, w/v) | Solubility (mg/ml) |
| --- | --- | --- | --- |
| 1 | 0 | 0.5 | 0.0013 |
| 2 | 0 | 1.25 | 0.0031 |
| 3 | 0 | 2.5 | 0.0058 |
| 4 | 0 | 5 | 0.014 |
| 5 | 0 | 10 | 0.032 |
| 6 | 0 | 20 | 0.060 |
| 7 | 0 | 30 | 0.086 |
| 8 | 0 | 40 | 0.12 |

Figure 3:
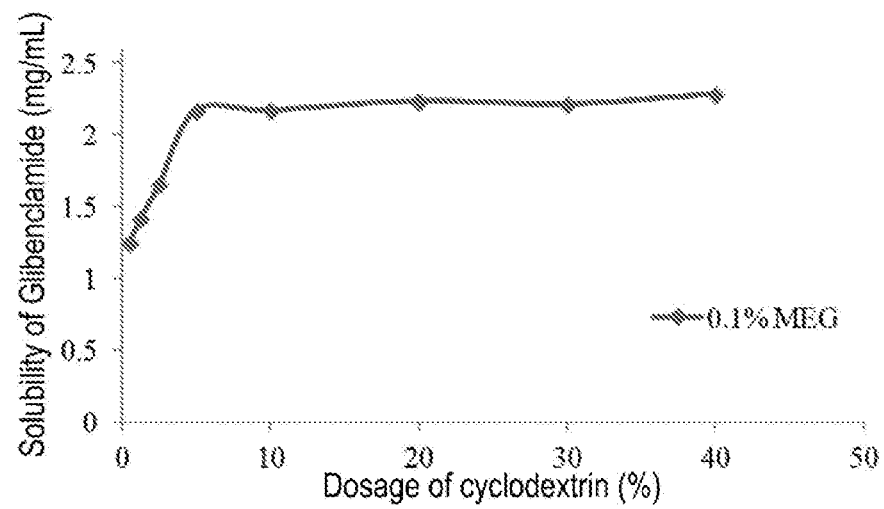

FIG. 3 is the solubility curve of glibenclamide in a solution comprising both 2-hydroxypropyl-β-cyclodextrin and meglumine (the concentration of meglumine is fixed at 0.1%), Table 6 is the corresponding solubility data. As can be seen from FIG. 3: the water solubility of glibenclamide can be significantly increased by cyclodextrin and meglumine used in combination. When the concentration of meglumine is 0.1% (w/v) and the concentration of cyclodextrin ranges from 0.5% (w/v) to 5% (w/v), as the water solubility of glibenclamide at 25° C. is from 1.25 mg/ml to 2.17 mg/ml. When the concentration of cyclodextrin continues increasing from 5% (w/v) to 40% (w/v), the solubility of glibenclamide remains at about 2.17 mg/ml.

TABLE 6

| No. | Concentration of meglumine (%, w/v) | Concentration of cyclodextrin (%, w/v) | Solubility (mg/ml) |
| --- | --- | --- | --- |
| 1 | 0.1 | 0.5 | 1.25 |
| 2 | 0.1 | 1.25 | 1.42 |
| 3 | 0.1 | 2.5 | 1.66 |
| 4 | 0.1 | 5 | 2.17 |
| 5 | 0.1 | 10 | 2.17 |
| 6 | 0.1 | 20 | 2.23 |
| 7 | 0.1 | 30 | 2.21 |
| 8 | 0.1 | 40 | 2.28 |

Figure 4:
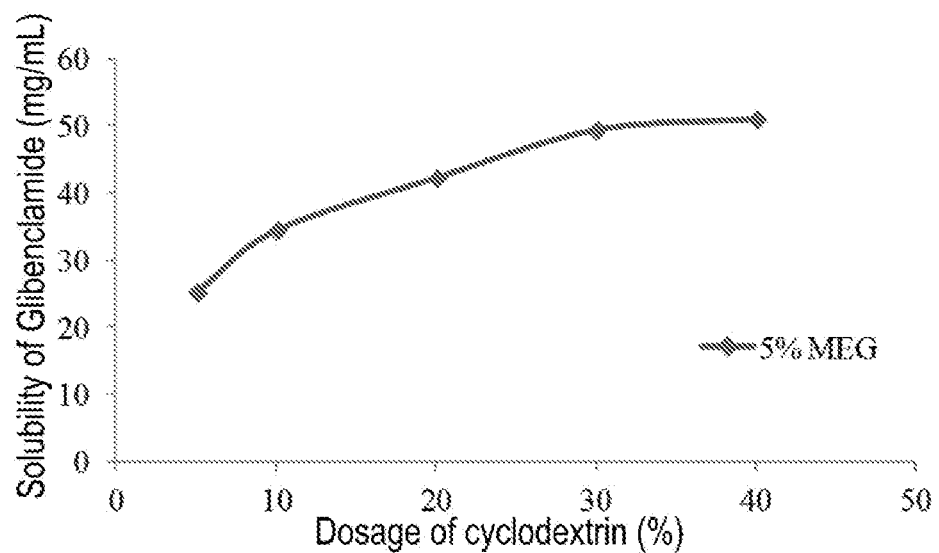

FIG. 4 is the solubility curve of glibenclamide in a solution comprising both 2-hydroxypropyl-β-cyclodextrin and meglumine (the concentration of meglumine is fixed at 5%), Table 7 is the corresponding solubility data. As can be seen from FIG. 4: the water solubility of glibenclamide can be significantly increased by cyclodextrin and meglumine used in combination. When the concentration of meglumine is 5% (w/v) and the concentration of cyclodextrin ranges from 5% (w/v) to 30% (w/v), the water solubility of glibenclamide at 25° C. is from 25.23 mg/ml to 49.37 mg/ml. As the concentration of cyclodextrin continues increasing from 30% (w/v) to 40% (w/v), the solubility of glibenclamide remains at about 49.37 mg/ml.

TABLE 7

| No. | Concentration of meglumine (%, w/v) | Concentration of cyclodextrin (%, w/v) | Solubility (mg/ml) |
| --- | --- | --- | --- |
| 1 | 5 | 5 | 25.23 |
| 2 | 5 | 10 | 34.45 |
| 3 | 5 | 20 | 42.25 |
| 4 | 5 | 30 | 49.37 |
| 5 | 5 | 40 | 50.99 |

It was demonstrated from the results of FIGS. 1~4 and Tables 4~7 that meglumine and cyclodextrin in combination produced an unexpected synergistic effect on the improved solubility of glibenclamide. The introduce of meglumine may promote the inclusion effect of cyclodextrin with glibenclamide, further increasing the solubility of glibenclamide. It was demonstrated from the results of FIGS. 3~4 that the promoting effect of meglumine on the inclusion effect of cyclodextrin with glibenclamide may be related to the concentration of meglumine.

Figure 5:
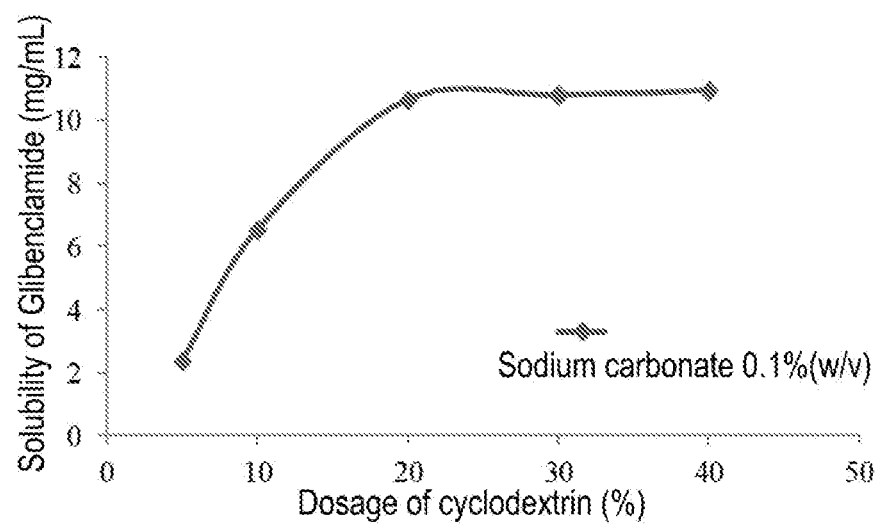

FIG. 5 is the solubility curve of glibenclamide in a solution comprising both 2-hydroxypropyl-β-cyclodextrin and sodium carbonate (the concentration of sodium carbonate is fixed at 0.1%), Table 8 is the corresponding solubility data. As can be seen from FIG. 5, the water solubility of glibenclamide can be significantly increased by cyclodextrin and sodium carbonate used in combination. When the concentration of sodium carbonate is 0.1% (w/v) and the concentration of cyclodextrin ranges from 5% (w/v) to 20% (w/v), the water solubility of glibenclamide at 25° C. is 2.35 mg/ml to 10.63 mg/ml. When the concentration of cyclodextrin continues increasing from 20% (w/v) to 40% (w/v), the solubility of glibenclamide remains at about 10.63 mg/ml.

TABLE 8

| No. | Concentration of sodium carbonate (%, w/v) | Concentration of cyclodextrin (%, w/v) | Solubility (mg/ml) |
| --- | --- | --- | --- |
| 1 | 0.1 | 5 | 2.35 |
| 2 | 0.1 | 10 | 6.51 |
| 3 | 0.1 | 20 | 10.63 |
| 4 | 0.1 | 30 | 10.78 |
| 5 | 0.1 | 40 | 10.91 |

Figure 6:
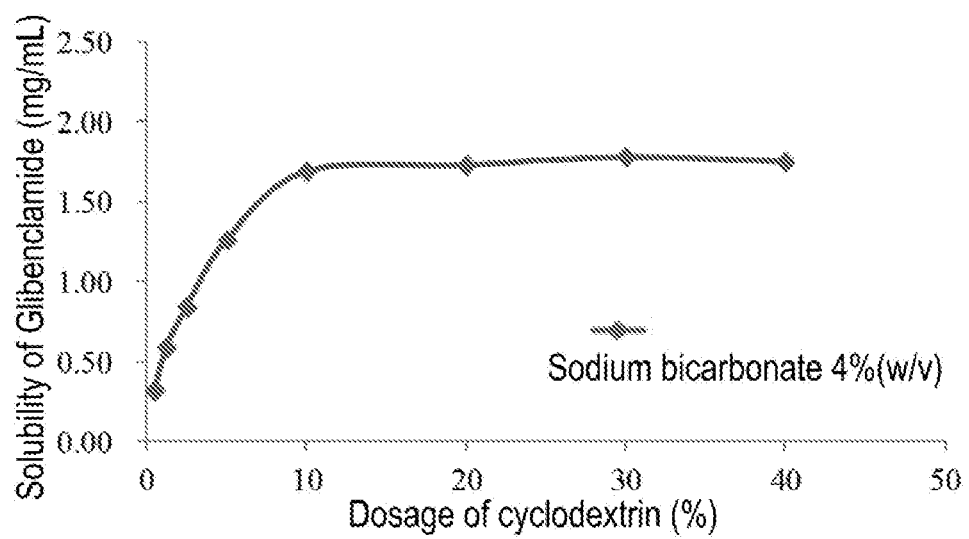

FIG. 6 is the solubility curve of glibenclamide in a solution comprising both 2-hydroxypropyl-β-cyclodextrin and sodium hydrogen carbonate (the concentration of sodium hydrogen carbonate is fixed at 4%), Table 9 is the corresponding solubility data. As can be seen from FIG. 6, the water solubility of glibenclamide can be significantly increased by cyclodextrin and sodium hydrogen carbonate used in combination. When the concentration of sodium hydrogen carbonate is 4% (w/v) and the concentration of cyclodextrin ranges from 0.5% (w/v) to 10% (w/v), the water solubility of glibenclamide at 25° C. is 0.32 mg/ml to 1.69 mg/ml. When the concentration of cyclodextrin continues increasing from 10% (w/v) to 40% (w/v), the solubility of glibenclamide remains at about 1.69 mg/ml.

TABLE 9

| No. | Concentration of sodium hydrogen carbonate (%, w/v) | Concentration of cyclodextrin (%, w/v) | Solubility (mg/ml) |
| --- | --- | --- | --- |
| 1 | 4 | 0.5 | 0.32 |
| 2 | 4 | 1.25 | 0.59 |
| 3 | 4 | 2.5 | 0.84 |
| 4 | 4 | 5 | 1.26 |
| 5 | 4 | 10 | 1.69 |
| 6 | 4 | 20 | 1.73 |
| 7 | 4 | 30 | 1.78 |
| 8 | 4 | 40 | 1.75 |

Figure 7:
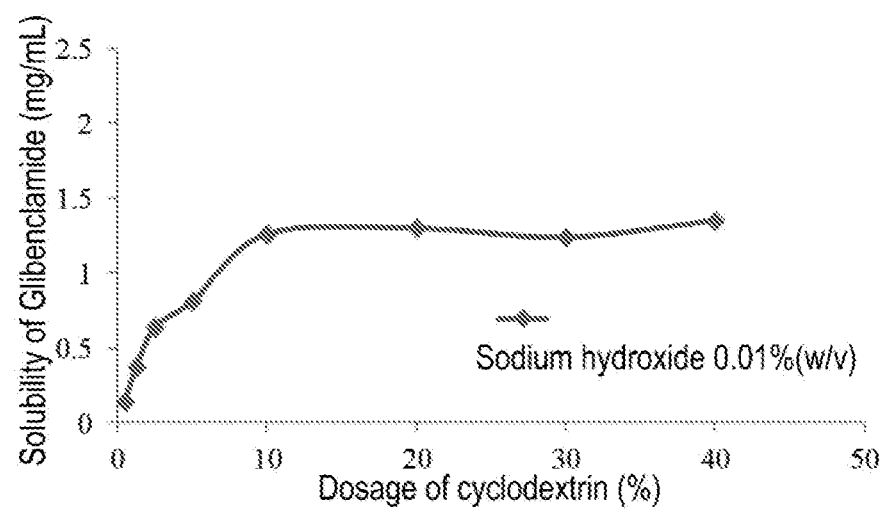

FIG. 7 is the solubility curve of glibenclamide in a solution comprising both 2-hydroxypropyl-β-cyclodextrin and sodium hydroxide (the concentration of sodium hydroxide is fixed at 0.01%), Table 10 is the corresponding solubility data. As can be seen from FIG. 7, the water solubility of glibenclamide can be significantly increased by cyclodextrin and sodium hydroxide used in combination. When the concentration of sodium hydroxide is 0.01% (w/v) and the concentration of cyclodextrin ranges from 0.5% (w/v) to 10% (w/v), the water solubility of glibenclamide at 25° C. is respectively 0.14 mg/ml to 1.26 mg/ml. The concentration of cyclodextrin continues increasing from 10% (w/v) to 40% (w/v), the solubility of glibenclamide remains at about 1.26 mg/ml.

TABLE 10

| No. | Concentration of sodium hydroxide (%, w/v) | Concentration of cyclodextrin (%, w/v) | Solubility (mg/ml) |
| --- | --- | --- | --- |
| 1 | 0.01 | 0.5 | 0.14 |
| 2 | 0.01 | 1.25 | 0.37 |
| 3 | 0.01 | 2.5 | 0.64 |
| 4 | 0.01 | 5 | 0.81 |
| 5 | 0.01 | 10 | 1.26 |
| 6 | 0.01 | 20 | 1.30 |
| 7 | 0.01 | 30 | 1.24 |
| 8 | 0.01 | 40 | 1.35 |

It was demonstrated from the results of FIGS. 1~7 and Tables 4~10 that both the additive (e.g., meglumine, sodium carbonate, sodium hydrogen carbonate or sodium hydroxide) and cyclodextrin brought about an unexpected synergistic effect on the increasing solubility of glibenclamide. The introduce of the additive may promote the inclusion effect of cyclodextrin with glibenclamide, further increasing the solubility of glibenclamide. It was demonstrated from the results of FIGS. 3~7 that the promoting effect of the additive on the inclusion effect of cyclodextrin with glibenclamide may be related to the concentration of the additive.

TEST EXAMPLE 4 pH Adjusting Test

The stabilities of different glibenclamide pharmaceutical compositions at different pH were investigated.

With reference to the method in Example 1, pharmaceutical compositions were prepared according to the formula in Table 11, wherein the concentration of glibenclamide was fixed at 1 mg/ml. The solutions formulated according to each formula were divided into three equal parts, and the pH of the three parts of the solutions was respectively adjusted to 7.0, 7.5 and 8.0 with 0.1M hydrochloric acid, obtaining solutions of glibenclamide pharmaceutical compositions with different pH. The above solutions of glibenclamide pharmaceutical compositions with different pH were left at 25 C., and the conditions regarding precipitates in the solutions were observed.

Test results were shown in Table 11, when the solution of the pharmaceutical composition only comprising 0.1% (w/v) meglumine was adjusted to pH 7.5 with 0.1M hydrochloric acid, the drug precipitates appeared; after the solution of the composition adjusted to a pH of 8.0 and was left for 24 h, white precipitates appeared. However, when the solution of the composition comprising 0.1% (w/v) meglumine and different concentration of cyclodextrin was adjusted to a pH of 8.0 and left for 96 h, no precipitate was detected. When the solution of the composition comprising 0.1% (w/v) meglumine and 1.25% cyclodextrin was adjusted to a pH of 7.5 and left for 96 h, only very few drug crystals were precipitated; when the solution of the composition comprising 0.1% (w/v) meglumine and 2.50% cyclodextrin was adjusted to a pH of 7.0 and left for 96 h, only very few drug crystals were precipitated; when the solution of the composition comprising 0.1% (w/v) meglumine and 5.0% cyclodextrin was adjusted to pH 7.0 and left for 96 h, no drug crystals were precipitated. It was demonstrated from the above results that cyclodextrin in the composition has the effects of inhibiting the precipitation of glibenclamide and establishing the solution of pharmaceutical composition.

TABLE 11

| Formula | pH | 0 h | 24 h | 48 h | 72 h | 96 h |
|---|---|---|---|---|---|---|
| GB + 0.1% meglumine | 8.0 | − | + | ++ | +++ | ++++ |
|  | 7.5 | ++++ | ++++ | ++++ | ++++ | ++++ |
|  | 7.0 | ++++ | ++++ | ++++ | ++++ | ++++ |
| GB + 0.1% meglumine + 1.25% cyclodextrin | 8.0 | − | − | − | − | − |
|  | 7.5 | − | − | − | − | + |
|  | 7.0 | − | + | + | + | + |
| GB + 0.1% meglumine + 2.50% cyclodextrin | 8.0 | − | − | − | − | − |
|  | 7.5 | − | − | − | − | − |
|  | 7.0 | − | − | − | − | + |
| GB + 0.1% meglumine + 5% cyclodextrin | 8.0 | − | − | − | − | − |
|  | 7.5 | − | − | − | − | − |
|  | 7.0 | − | − | − | − | − |

Note:
GB: glibenclamide, −: there was no precipitates; +~++++: there were precipitates, and the more +, the more precipitates.

TEST EXAMPLE 5

Test of Adsorption in an Infusion Bag 5.1 Comparison on cyclodextrin and additive used in combination and the additive used alone The compositions of Examples 2, 8 and 9 were respectively diluted with 0.9% solution of sodium chloride (physiological saline) until the concentration of glibenclamide was 5 µg/ml, the resulting solutions numbered as 5a, 5b, 5c. At the same time, the corresponding injectable composition without hydroxypropyl-β-cyclodextrin was prepared according to the formula in Table 12, diluted with 0.9% solution of sodium chloride until the concentration of glibenclamide was 5 µg/ml, numbering as 5a', 5b', 5c'. The drug solution after dilution was divided into two parts, one injected into a PVC infusion bag, placed at 25° C., and shaken at 100 rpm; the other placed in a measuring flask at 25° C., and shaken at 100 rpm (as the control). Sampling after 96 hours, and the area of the main drug peak was determined by HPLC method (Agilent Eclipse XDB-C18 column (5 µm, 4.6×250 mm); the mobile phase is methanol: 50 mM ammonium dihydrogen phosphate (volume ratio) =72.5:27.5 (pH adjusted to 3.5±0.1 with 2% phosphoric acid); the detecting wavelength is 300 nm; the flow rate of the mobile phase is 1 ml/min; sample amount 20µl. With the drug solution in the measuring flask as the control, the drug adsorption ratio was calculated (drug adsorption ratio=100× (the area of the peak of the main drug in the measuring flask—the area of the peak of the main drug in the PVC infusion bag)/the area of the peak of the main drug in the measuring flask).

Test results were shown in Table 12: for 3 drug solutions (5a', 5b', 5c') of low concentrations without hydroxypropyl-β-cyclodextrin, there were all significant drug adsorption in the PVC infusion bags, with the adsorption ratios higher than 10%, and the concentration of drugs significantly lowered. However, for the corresponding drug solutions (5a, 5b, 5c) of low concentrations comprising hydroxypropyl-β-cyclodextrin, no significant drug adsorptions were detected in the PVC infusion bags, with the adsorption ratios lower than 0.1%. It was demonstrated from the above results that cyclodextrin in the composition may significantly inhibit the adsorption of the PVC infusion bag to the drugs.

TABLE 12

| Groups | Formula | Adsorption ratio (%) |
|---|---|---|
| 5a' | 1.0 mg/ml GB + 0.1% meglumine | 17.33 |
| 5a | 1.0 mg/ml GB + 0.1% meglumine + 5.0% hydroxypropyl-β-cyclodextrin | 0.07 |
| 5b' | 1.0 mg/ml GB + 0.2% sodium hydroxide | 21.19 |
| 5b | 1.0 mg/ml GB + 0.2% sodium hydroxide + 5.0% hydroxypropyl-β-cyclodextrin | 0.04 |
| 5c' | 2.0 mg/ml GB + 0.1% sodium carbonate | 14.66 |
| 5c | 2.0 mg/ml GB + 0.1% sodium carbonate + 5.0% hydroxypropyl-β-cyclodextrin | 0.06 |

5.2 Comparison of the adsorption effects of different cyclodextrins to the drug

According to the formulas of Table 13, 14, the additive and the cyclodextrin were dissolved in 50~70 ml water, into which was then added glibenclamide, with stirring to dissolve, made to 100 ml, obtaining the pharmaceutical compositions (groups 5d~5i).

The composition solutions in groups 5e and 5f were adjusted to a pH of 8.0, obtaining the pharmaceutical compositions (groups 5j and 5k), the formulas of which were shown in Table 15.

The pharmaceutical composition of each group 5d~5k was diluted by 500 times with 0.9% solution of sodium chloride, making the concentration of glibenclamide to 2 µg/ml. The drug solution after dilution was divided into two parts, one injected into a PVC infusion bag, placed at 25° C., and shaken at 100 rpm; the other placed in a measuring flask at 25° C., and shaken at 100 rpm (as the control). The adsorption ratios of the drugs were determined according to the method in 5.1.

TABLE 13

| Group | Formula | Adsorption ratio after 24 h (%) | Adsorption ratio after 48 h (%) |
|---|---|---|---|
| 5d | 1 mg/ml GB + 1% sodium carbonate (no cyclodextrin) | 4.7% | 8.5% |
| 5e | 1 mg/ml GB + 1% sodium carbonate + 5% sulfobutyl ether-β-cyclodextrin | 2.4% | 4.6% |
| 5f | 1 mg/ml GB + 1% sodium carbonate + 5% hydroxypropyl-β-cyclodextrin | −2.7% | −3.3% |

TABLE 14

| Group | Formula | Adsorption ratio after 96 h (%) |
|---|---|---|
| 5g | 1 mg/ml GB + 0.5% sodium carbonate (no cyclodextrin) | 15.0% |
| 5h | 1 mg/ml GB + 0.5% sodium carbonate + 5% sulfobutyl ether-β-cyclodextrin | 8.2% |
| 5i | 1 mg/ml GB + 0.5% sodium carbonate + 5% hydroxypropyl-β-cyclodextrin | 3.7% |

TABLE 15

| Group | Formula | pH | Adsorption ratio after 72 h (%) |
|---|---|---|---|
| 5j | 1 mg/ml GB + 1.0% sodium carbonate + 5% sulfobutyl ether-β-cyclodextrin | 8.0 | 5.67% |
| 5k | 1 mg/ml GB + 1.0% sodium carbonate + 5% hydroxypropyl-β-cyclodextrin | 8.0 | 2.08% |

It was demonstrated from the results of Table 13~15 that, compared with the pharmaceutical composition without cyclodextrin, the pharmaceutical composition of the present disclosure comprising an additive and a cyclodextrin can significantly inhibit the adsorption of the PVC infusion bag to the drugs. And the inhibition effect of hydroxypropyl-β-cyclodextrin on the adsorption was better than that of sulfobutyl ether-β-cyclodextrin.

TEST EXAMPLE 6

Comparison of the Buffer Capacities of Cyclodextrin to Prevent the Drugs from Precipitating According to the method of Test Example 5, the pharmaceutical compositions (groups 5g, 5h and 5i) were prepared, into which were respectively added 0.1M hydrochloric acid until there were precipitates being detected. The formulas and experimental results were shown in Table 16.

TABLE 16

| Group | Formula | Initial pH | pH when precipitates were detected |
|---|---|---|---|
| 5g | 1 mg/ml GB + 0.5% sodium carbonate | 11.48 | 8.33 |
| 5h | 1 mg/ml GB + 0.5% sodium carbonate + 5% sulfobutyl ether-β-cyclodextrin | 10.05 | 7.25 |
| 5i | 1 mg/ml GB + 0.5% sodium carbonate + 5% hydroxypropyl-β-cyclodextrin | 9.89 | 6.27 |

It was shown from the results that, the initial pH of the above three groups of pharmaceutical composition solutions were 10~11. When the glibenclamide precipitates were detected, the pH of the solutions of groups 5g, 5h and 5i were respectively 8.33, 7.25 and 6.27. This indicates that the pharmaceutical compositions of the present disclosure have buffer capacities capable of preventing glibenclamide from precipitating, and the buffer capacity of hydroxypropyl-β-cyclodextrin for preventing glibenclamide from precipitating was a little better than that of sulfobutyl ether-β-cyclodextrin.

TEST EXAMPLE 7

Study of Pharmacology in Rat MCAO Models 7.1. Experiment specification: All the animal experiment operations in the test were performed under the regulations of IACUC (Institutional Animal Care and Use Committee) of the experiment institution and conformed to the principles of AAALAC (Association for Assessment and Accreditation of Laboratory Animal Care).

7.2 Experiment Animals: Male Sprague-Dawley (SD) rat, clean grade, weighing at 200~230 g. The temperature of animal feeding room was maintained at 20~24° C., the humidity was maintained at 30~70%; a cycle of lighting on 12 hours/lighting off 12 hours (06:00 AM on, 18:00 PM off) every day was employed. During the experiment, the animals were feed separately, and had free access to water and food.

7.3. Testing drugs

The test drugs in group GB was formulated as follows: glibenclamide was dissolved in a little DMSO (dimethyl sulfoxide), the resulting solution was diluted to a DMSO concentration of 5 vol % with physiological saline, and the pH of the solution was adjusted to 8~8.5 with NaOH. By means of the above process, solutions with glibenclamide concentration of 200 µg/ml and 10 µg/ml were respectively formulated.

The test drugs in group H-GB was formulated as follows: Taking the lyophilized product of Example 13, into which was added an appropriate amount of physiological saline and respectively formulated into a solution with a glibenclamide concentration of 200 µm/ml, 10 µm/ml.

7.4 Establishment of MCAO model (middle cerebral artery occlusion)

Rats were rested for about 1 week before the experiment started. On the day of the experiment, the surgical tools were sterilized by autoclaving. The rats were anesthetized by intraperitoneally injecting chloral hydrate (330 mg/kg). The common carotid artery and external carotid artery of the rats were separated, and a sterilized MCAO monofilament was used to insert into the internal carotid artery through the opening of the external carotid artery to a depth of about 18 mm, until the head of the monofilament reached the starting part of the middle cerebral artery, the opening of the external carotid artery was ligatured to fix the monofilament. After 1.5 hours, a reperfusion step was performed, that is, the monofilament was pulled out and stopped when there was a certain hindrance at the intersection between the external carotid artery and the common carotid artery. The blood flow in the brain was monitored with a laser Doppler (Model moorVMS-LDF2, Manufacturer moor) respectively pre-operation, post-operation and immediately after reperfusion, and the molding in which the ratio of the postoperative blood flow to the preoperative blood flow was less than 30% was regarded as a qualified molding.

Postoperative care: The rats were placed on a warming blanket immediately after the operation, and subcutaneously injected with meloxicam (2 mg/kg) for analgesia, and intraperitoneally injected with gentamicin (6 mg/kg).

7.5 Animal Groups and Dosing 24 animals were randomly divided into 3 groups based on their weights, 8 per group (n=8). As shown in Table 17.

TABLE 17

| Group | n | Dosing dosage | Dosing route | Dosing time |
|---|---|---|---|---|
| Control | 8 | — | ip + sc | Postischemia 4 h + 44 h |
| GB | 8 | 10 µg/ml + 200 ng/h | ip + sc | Postischemia 4 h + 44 h |
| H-GB | 8 | 10 µg/ml + 200 ng/h | ip + sc | Postischemia 4 h + 44 h |

Intraperitoneally injection administration (intra-peritoneally, ip): glibenclamide 10 µg/kg (dosing volume 1 ml/kg, concentration of drug 10 µg/ml).

Continuous subcutaneous administration (subcutaneous, sc): glibenclamide 200 ng/h (dosing volume 1 µl/h, 100 µl/osmotic pump/rat, concentration of drug in the pump 200 µg/ml); the osmotic pump is ALZET osmotic pump 1003D, whose manufacturer is DURECT Corporation.

The testing drugs in the control were replaced with physiological saline; the dosing volume of intra-peritoneally injection was 1 ml/kg, the dosing volume of continuous subcutaneous administration was 1 μl/h (100 μl/osmotic pump/rat).

Intra-peritoneally injection administration was carried out at ischemia 4 h, the osmotic pump was implanted subcutaneously, and the subcutaneous administration was continued for 44 hours. The implantation of the osmotic pump was that a small incision was made in the skin between the scapula, and then the skin and the subcutaneous connective tissue were separated with hemostatic forceps, forming a small pouch, into which was inserted the osmotic pump, with the flow regulator being inwards, and the opening in the skin can be sewed or clamped with a clamp.

7.6 Neurobehavioral Scoring:

Neurobehavioral scorings were performed at ischemia 24 h, 48 h. Longa Scoring, the neurological examination was divided into 5 grades, score 0: normal, with no neurologic impairment; score 1: the left forepaw can't fully extend, mild neurologic impairment; score 2: rats will turn around to the left (paralytic side) when walking, moderate neurologic impairment; score 3: rats will fall down to the left (paralytic side) when walking, severe neurologic impairment; score 4: incapable of walking spontaneously, with loss of consciousness. The effect of drugs on the neurobehavioral scores of MCAO rats were seen in Table 18.

TABLE 18

| Group | n | 24 h | 48 h |
| --- | --- | --- | --- |
| Control | 8 | 2.63 ± 0.18 | 2.25 ± 0.25 |
| GB | 8 | 1.75 ± 0.25 | 2.00 ± 0.19 |
| H-GB | 8 | 1.63 ± 0.18 | 1.88 ± 0.23 |

It was shown from the results of Table 18 that, compared with the control, there were declines of the neurobehavioral scores in both group GB and group H-GB at 24 h, 48 h, indicating that both group GB and group H-GB could improve the neurobehavioral impairments of MCAO rats. There was a significant decline of the score in group H-GB, indicating that the injection pharmaceutical composition of the present disclosure may significantly improve the neurological score of rats with cerebral infarction.

7.7 Area and swelling degree of cerebral infarction:

After ischemia for 48 hours, the brain was taken and put into a brain slicer to slice coronal sections through the brain (2 mm each piece), stained at dark with 1% TTC for 15 min at 37° C., and analyzed for the area of infarction after taking a photograph. The proportion of the infarction area was defined as the ratio of the area of infarction region/total area of the brain, the swelling degree was defined as the proportion of the area of infarction side hemisphere with respect to the area of non-infarction side hemisphere. The effect of drugs on the infarction area and the brain swelling degree of MCAO rats were seen from Table 19.

TABLE 19

| Group | n | Proportion of the infarction area (%) | Swelling degree |
| --- | --- | --- | --- |
| Control | 8 | 31.11 ± 1.38 | 1.35 ± 0.04 |
| GB | 8 | 18.41 ± 2.54 | 1.31 ± 0.04 |
| H-GB | 8 | 18.49 ± 2.27 | 1.32 ± 0.05 |

It was shown from the results that, compared with the control group, there were very significant reductions of the brain infarction area in group GB and group H-GB. There was no statistical significance in the comparison of the brain swelling degrees of rats in each group. It was demonstrated from the result of this test example that, the pharmaceutical composition of the present disclosure had not produced any negative effects on the potency of sulfonylurea drug s in the arterial acute ischemia reperfusion models of rat brains, and not produced negative effects on getting through the blood brain barrier for the sulfonylurea drug.

TEST EXAMPLE 8

Reconstitution of Lyophilized Products

The lyophilized product in one vial of Example 14 was dissolved with 1 ml water for injection (water that conforms to the specification of the item of water for injection in Pharmacopoeia of People's Republic of China), and the pH of the solution after reconstitution was determined as 8.8.

It was demonstrated from Test Example 8 that there was no difference between the pH of the resulting solution after the reconstitution of the lyophilized products and the PH of the solution before the lyophilization. In Example 14, glycine was employed as the pH regulator, with the pH of the resulting pharmaceutical injection in the general pH ranges (4~9).

In conclusion, with regard to the sulfonylurea drug injectable composition provided in the present disclosure, the solubility and the stability of the sulfonylurea drug in water were greatly enhanced by cyclodextrin and the additive used in combination, compared with those achieved by using the cyclodextrin alone or using the additive alone, and the adsorption of the PVC infusion bag to the drug could be significantly inhibited. The pharmaceutical composition has the benefits of simple formula, low cost, easy to operate, stable and controllable quality, and good reproducibility.

The invention claimed is:

1. A pharmaceutical composition for injection administration, comprising a sulfonylurea drug, a cyclodextrin and an additive;
    wherein said cyclodextrin is 2-hydroxypropyl-β-cyclodextrin and said additive is selected from sodium hydroxide, sodium carbonate, sodium hydrogen carbonate, and meglumine.

2. The pharmaceutical composition according to claim 1, wherein the pharmaceutical composition has a weight ratio of said sulfonylurea drug to said additive of 1:0.5~100; and
    wherein the pharmaceutical composition has a weight ratio of said sulfonylurea drug to said cyclodextrin of 1:25~1000.

3. The pharmaceutical composition according to claim 2, wherein the pharmaceutical composition has a weight ratio of said sulfonylurea drug to said additive of 1:1~100.

4. The pharmaceutical composition according to claim 2, wherein the pharmaceutical composition has a weight ratio of said sulfonylurea drug to said cyclodextrin of 1:50~1000.

5. The pharmaceutical composition according to claim 1, wherein the pharmaceutical composition has a weight ratio of said sulfonylurea drug:said additive:said cyclodextrin of 1:0.05~100:0.2~1000.

6. The pharmaceutical composition according to claim 1, wherein said sulfonylurea drug is selected from glibenclamide, gliclazide, glipizide, gliquidone, glibornuride, glimepiride, glisoxepide, acetohexamide, glycyclamide, glisamuride, glisentide, glisolamide, glyoctamide, chlorpropamide, tolazamide, tolbutamidum, repaglinide and nateglinide.

7. The pharmaceutical composition according to claim 1, further comprising glucose, sodium chloride, a lyophilization additive, a pH regulator and/or water.

8. The pharmaceutical composition according to claim 1, wherein the pharmaceutical composition is an injectable solution or a powder injection.

9. The pharmaceutical composition according to claim 8, wherein the pharmaceutical composition is an aqueous injectable solution.

10. The pharmaceutical composition according to claim 9, wherein one or more of said following is satisfied:
    a) said pharmaceutical composition comprises an additive at a concentration of 0.01~0.5% (w/v), said cyclodextrin at a concentration of 0.5~10% (w/v), a sulfonylurea drug at a concentration of less than or equal to the saturation concentration of said sulfonylurea drug in said injectable solution;
    b) said pharmaceutical composition comprises an additive at a concentration of 1~10% (w/v), said cyclodextrin at a concentration of 1~30% (w/v), a sulfonylurea drug at a concentration of less than or equal to the saturation concentration of said sulfonylurea drug in said injectable solution.

11. The pharmaceutical composition according to claim 8, said pharmaceutical composition has a pH of 5~11.

12. A method for preparing the pharmaceutical composition according to claim 1, comprising following steps:
    a) dissolving the additive and the cyclodextrin in a solvent;
    b) adding the sulfonylurea drug into the product of step a), mixing by stirring;
    c) optionally, adding a lyophilization additive into the product of step b), and adjusting pH;
    d) subjecting the product of step b) or step c) to sterilization,
    optionally, drying the product of step d) to obtain the composition.

13. A method for the therapeutic treatment of encephaledema in acute stroke, traumatic brain injury, or in spinal cord injury, and of type I diabetes or type II diabetes, comprising administering to a subject in need thereof a therapeutically effective amount of the pharmaceutical composition according to claim 1;
    wherein said sulfonylurea drug is glibenclamide;
    wherein said cyclodextrin is 2-hydroxypropyl-β-cyclodextrin.

14. The pharmaceutical composition according to claim 1, wherein said additive is sodium hydrogen carbonate and/or sodium hydroxide.

15. The pharmaceutical composition according to claim 1, wherein said additive is sodium carbonate.

16. The pharmaceutical composition according to claim 1, wherein said additive is meglumine.

* * * * *